US011766503B1

(12) United States Patent
Jackson (10) Patent No.: US 11,766,503 B1
(45) Date of Patent: Sep. 26, 2023

(54) DISINFECTING HVAC SYSTEM AND METHODS OF MAKING AND USING THE SAME

(71) Applicant: Warren I. Jackson, Wilmington, NC (US)

(72) Inventor: Warren I. Jackson, Wilmington, NC (US)

( * ) Notice: Subject to any disclaimer, the term of this patent is extended or adjusted under 35 U.S.C. 154(b) by 0 days.

(21) Appl. No.: 18/076,507

(22) Filed: Dec. 7, 2022

(51) Int. Cl.
*A61L 9/20* (2006.01)

(52) U.S. Cl.
CPC .............. *A61L 9/20* (2013.01); *A61L 2209/12* (2013.01); *A61L 2209/14* (2013.01); *A61L 2209/16* (2013.01)

(58) Field of Classification Search
CPC .... A61L 9/20; A61L 2209/12; A61L 2209/14; A61L 2209/16
See application file for complete search history.

(56) References Cited

U.S. PATENT DOCUMENTS

| | | | |
|---|---|---|---|
| 2018/0361007 A1* | 12/2018 | Caffrey | A61L 9/20 |
| 2022/0135235 A1* | 5/2022 | Space | B64D 13/00 |
| | | | 250/436 |
| 2022/0170661 A1* | 6/2022 | Bonzani, Jr. | B03C 3/011 |

* cited by examiner

*Primary Examiner* — Sean E Conley
*Assistant Examiner* — Brendan A Hensel
(74) *Attorney, Agent, or Firm* — Ashley D. Johnson; Dogwood Patent and Trademark Law (57) ABSTRACT

The invention is a disinfecting HVAC system that combines thermal displacement ventilation technology with UV-C light technology to isolate, concentrate, and/or kill harmful microorganisms (such as SARS-Cov-2) present in enclosed spaces. The system includes a single manifold collection pipe placed adjacent to the ceiling (e.g., about 12-14 feet above the floor). The collection pipe has a high collection efficiency when connected to an HVAC air handler and booster fan tandem. In the air handler, the warm air is cooled and treated with a sufficient dose of UV-C light to inactivate any microorganisms within a short amount of time. The UV-C treated air is then returned to the enclosed space through a plurality of low velocity diffusers.

20 Claims, 7 Drawing Sheets

DISINFECTING HVAC SYSTEM AND METHODS OF MAKING AND USING THE SAME

TECHNICAL FIELD

The presently disclosed subject matter is generally directed to a disinfecting heating, ventilation, and air conditioning (HVAC) system, and to methods of making and using the disclosed system.

BACKGROUND

It is increasingly becoming important for HVAC systems to implement measures to maintain acceptable air quality within homes and buildings, especially in view of the global COVID-19 pandemic. Current best practices recommended by the CDC for improved indoor air quality have been adopted by the American Society of Heating, Refrigeration, and Air-Conditioning Engineers (ASHRAE). These recommendations include HVAC operations with indoor air purge rates at a maximum; system modifications to allow running with no air recycle; high efficiency filtration; opening all windows, even in the winter; use of plug in HEPA filters, UVC towers, and electric heaters. These recommendations were made with the assumption that our March 2020 public health crisis would be over within two (2) years and hence, they were never intended to be long term solutions: they greatly increase the energy cost and carbon footprint associated with HVAC operations, compromise our goal of reaching net zero carbon emissions by 2050, and shorten the life of HVAC equipment.

Most HVAC systems filter particles from conditioned air (e.g., air that has been heated or cooled). However, current HVAC filtration systems are generally incapable of effectively removing many viruses and biological contaminants from the air. Some prior art HVAC systems have incorporated HEPA filters in an effort to filter viruses and biological contaminants. However, because of the HEPA filters, the HVAC systems have very low airflow and require high pressures to filter air at a sufficient rate. In addition, many existing HVAC systems are simply not capable of operating with HEPA filtration without expensive upgrades and maintenance. Even with the noted upgrades, HEPA filtration places excessive strain on and reduces operative lifetime of HVAC systems. It would therefore be beneficial to provide an improved HVAC system capable of disinfecting the air within an enclosed space while minimizing the HVAC carbon footprint, thereby improving the safety and quality of air. Specifically, the disclosed system and method can be used as a long-term solution to remove harmful microorganisms (especially viruses) that can be transmitted through the air.

SUMMARY

In some embodiments, the presently disclosed subject matter is directed to a disinfecting heating, ventilating, and cooling (HVAC) system. The system comprises a collection pipe defined by an interior passageway, a closed first end, an open second end, and a plurality of negative pressure nozzles positioned on a lower face of the collection pipe. At least one of the nozzles has a diameter that differs from at least one other nozzle. The system includes an air handler in fluid connection with the second end of the collection pipe, wherein the air handler comprises a UV-C light source, a filter, and heating/cooling coils. Air passing through the air handler is exposed to the UV-C light source, passes through the filter, and is heated or cooled. The system includes at least one fan in fluid connection with the air handler, wherein the at least one fan circulates air throughout the system. The system comprises a plurality of low velocity diffusers positioned in fluid connection with the at least one fan, wherein the low velocity diffusers are positioned in a floor of an enclosed space. The plurality of low velocity diffusers are aligned on each side of a pair of opposing walls in the enclosed space to create a plurality of air zones, and at least one nozzle is positioned within each air zone, adjacent to the ceiling of the enclosed space.

In some embodiments, air entering the collection pipe is disinfected after exposure to the UV-C light source, with a 4 log reduction in microorganisms present in the air.

In some embodiments, the microorganisms are selected from influenza virus, coronavirus (SARS-CoV), respiratory syncytial virus (RSV), adenovirus, cytomegalovirus (CMV), Epstein-Barr virus (EBV), dengue virus, rhinovirus, bacteria, or combinations thereof.

In some embodiments, the system includes a port that allows environmental air to be mixed with air exiting the collection pipe prior to entering the air handler.

In some embodiments, the system comprises an outlet that allows disinfected air to be exited from the system prior to entering the low velocity diffusers.

In some embodiments, the collection pipe is positioned about 5-15 feet above the floor.

In some embodiments, the collection pipe has a diameter of about 15-30 inches.

In some embodiments, each nozzle has a diameter of about 12-16 inches.

In some embodiments, each nozzle has a unique diameter compared to the other nozzles.

In some embodiments, the nozzles are uniformly distributed about the collection pipe.

In some embodiments, the UV-C light source has a wavelength of about 254 nm to 265 nm.

In some embodiments, the air filter is selected from one or more of polyethylene fibers, polypropylene fibers, fiberglass, polyester, activated charcoal, sorbent materials, electrostatic materials, or combinations thereof.

In some embodiments, the UV-C light source is selected from a UV-C bulb, a UV-C lamp, an LED light, or combinations thereof.

In some embodiments, the presently disclosed subject matter is directed to a method of disinfecting air in an enclosed space defined by a ceiling and a floor. Specifically, the method comprises routing air adjacent to the ceiling of the enclosed space into the collection pipe of the disclosed disinfecting HVAC system via the plurality of nozzles. The method includes routing the air from the collection pipe to the air handler and activating the UV-C light source to disinfect the air. The method further includes passing the disinfected air through the system and back into the enclosed space via the low velocity diffusers.

In some embodiments, the air is disinfected in about 0.1 seconds by the UV-C light source.

In some embodiments, the method further includes mixing the air leaving the collection pipe with outside air prior to routing the air to the air handler.

In some embodiments, the method further includes venting the disinfected air to the outside environment prior to routing the air to the low velocity diffusers.

BRIEF DESCRIPTION OF THE DRAWINGS

FIG. 1 is a schematic of a disinfecting HVAC system in accordance with some embodiments of the presently disclosed subject matter.

FIG. 2 is a perspective view of an enclosed space in accordance with some embodiments of the presently disclosed subject matter.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is directed to a disinfecting heating, ventilation, and air conditioning (HVAC) system that is configured to reduce or eliminate the transmission of one or more airborne microorganisms within an enclosed space. The term "disinfecting" refers to the killing, destroying, or otherwise disabling of one or more pathogenic microorganisms that cause diseases or infections (e.g., a 4 log reduction in microorganisms). In some embodiments, the term "disinfecting" can include sanitizing a surface (e.g., a 3 log reduction in one or more pathogenic microorganisms). The term "microorganism" includes any type of living organism so small in size that it is only visible with the aid of a microscope, including (but not limited to) bacteria, viruses, archaea, fungi, protozoans, mycoplasma, prions, parasitic organisms, and combinations thereof. For example, targeted microorganisms can include the influenza virus, coronavirus (SARS-CoV), respiratory syncytial virus (RSV), adenovirus, cytomegalovirus (CMV), Epstein-Barr virus (EBV), dengue virus, rhinovirus, bacteria (e.g., *Streptococcus spp., Escherichia coli, Pseudomonas aeruginosa, Haemophilus influenza, Klebsiella pneumoniae, Acinetobacter baumannii, Neisseria meningitidis, Staphylococcus aureus, Streptococcus pyogenes,* and *Streptococcus pneumoniae*), or combinations thereof. It should be appreciated that the above list is non-limiting.

Figure 1:
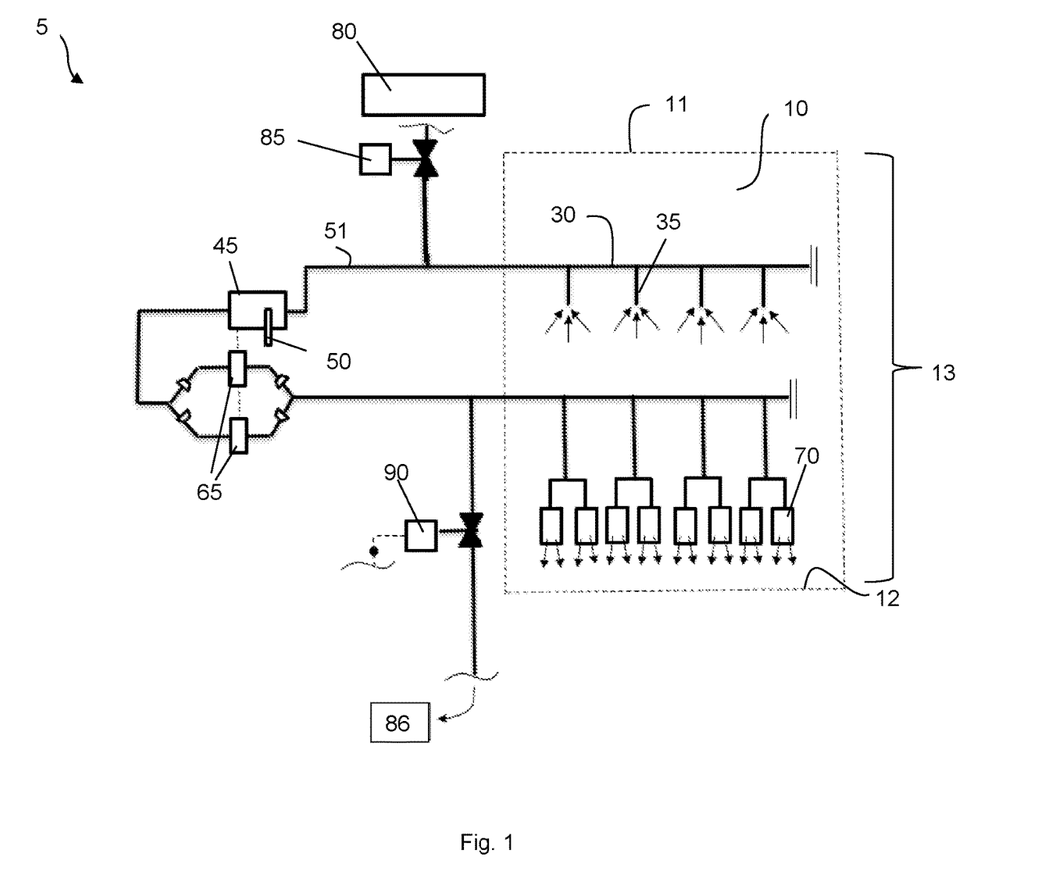

The disinfecting HVAC system combines thermal displacement ventilation technology with UV-C light technology to isolate, concentrate, and/or kill harmful microorganisms (such as SARS-Cov-2) present in enclosed spaces. The term "enclosed space" can include (but is not limited to) an interior room of a house, the interior of a house, the interior of a store, etc. As shown in the schematic of FIG. 1, in disinfecting HVAC system 5, UV-C-treated air is introduced into enclosed space 10 at floor level 12 using low velocity diffusers 70 to eliminate air mixing and to allow the development of a temperature gradient between the floor and ceiling 11. Occupants in the enclosed space expel air from their lungs at about 98° F. The warm expelled air migrates quickly towards ceiling 11, along with any harmful microorganism included in the warm air. The system includes single manifold collection pipe 30 placed adjacent to the ceiling (e.g., about 12-14 feet above the floor). The collection pipe has a high collection efficiency when connected to HVAC air handler 45 and booster fan tandem 65. In the air handler, the warm air is cooled and treated with a sufficient dose of UV-C light to inactivate any microorganisms within a short amount of time (e.g., about 0.01 seconds). The UV-C treated air is then returned to enclosed space 10 through a plurality of low velocity diffusers. If desired, fresh air makeup can be introduced into the enclosed space on demand to control $CO_2$ concentrations in the enclosed space.

Figure 2:
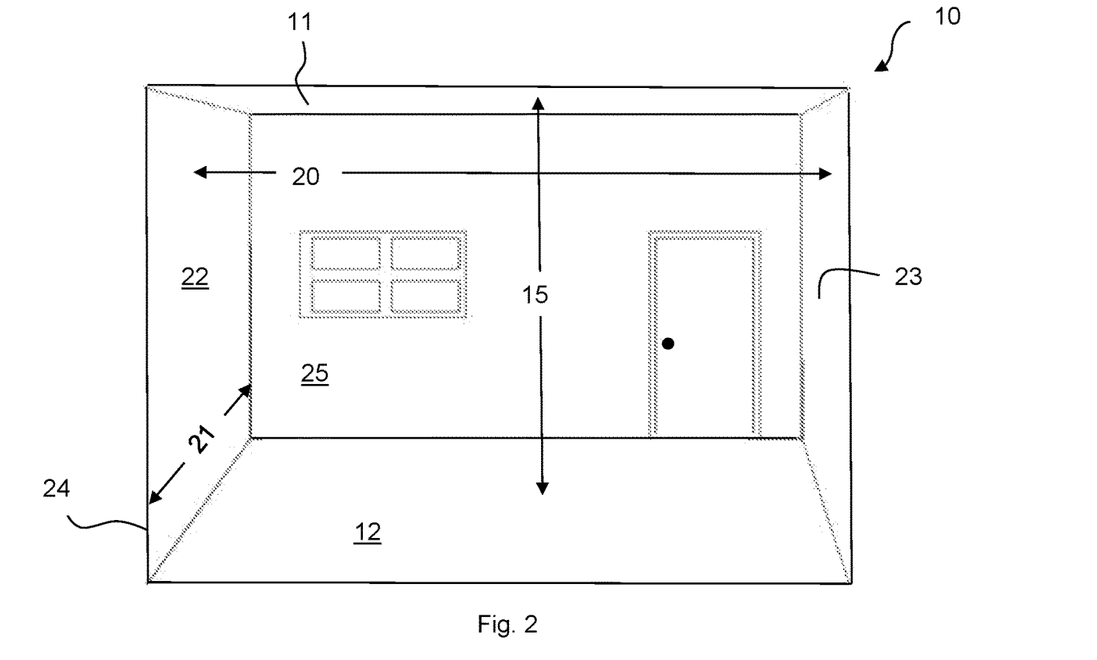

As shown in FIG. 2, enclosed space 10 can have any desired dimensions, such as height 15 of about 5-20 feet (e.g., at least/no more than about 5, 10, 15, 20 feet). The height includes the longest vertical distance between floor 12 and ceiling 11. The enclosed space can further have any desired length 20 and width 21, such as about 5-50 feet (e.g., at least/no more than about 5, 10, 15, 20, 25, 30, 35, 40, 45, 50 feet). The term "length" refers to the longest horizontal distance of the enclosed space, such as from first wall 22 to second wall 23. The term "width" refers to the longest straight-line distance perpendicular to the length (e.g., the distance between front and rear walls 24, 25). It should be appreciated that the enclosed space can include any optional features, such as doors, windows, cutouts, openings, and the like. It should further be appreciated that the ranges of length, width, and height of enclosed space 10 are not limited and the enclosed space have any desired dimensions.

Figure 3A:
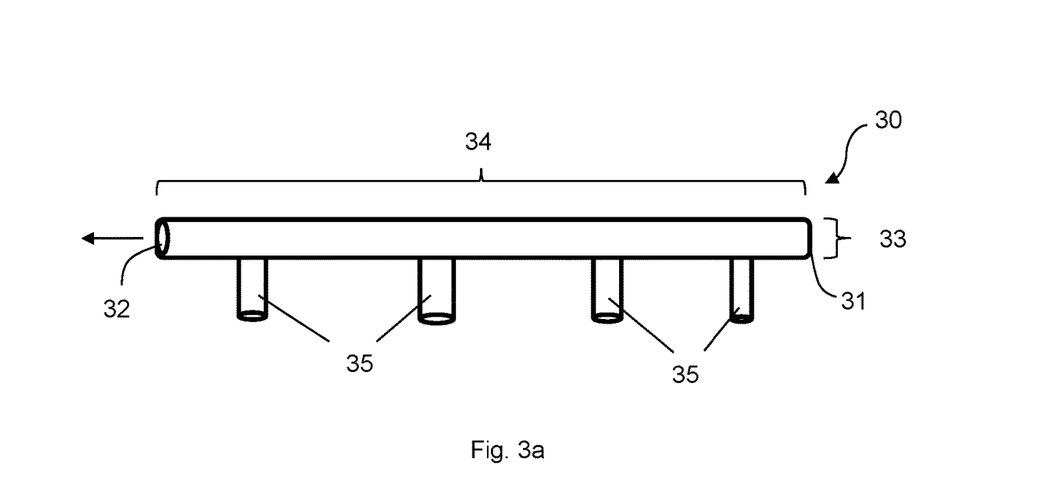
FIG. 3a is a perspective view of a collection pipe in accordance with some embodiments of the presently disclosed subject matter.

As noted above, system 5 includes manifold collection pipe 30 positioned to be centered at or near ceiling 11 of the disclosed space, as shown in FIG. 1. The term "manifold collection pipe" refers to a conduit that provides a fluid pathway for air. As illustrated in FIG. 3a, the pipe can include closed first end 31 and open second end 32 that allows air to be routed from the interior of enclosed space 10. The collection pipe also includes interior passageway 81 that provides a conduit for air being transported out of the enclosed space. In some embodiments, collection pipe 30 can be positioned about 5-15 feet above floor 12 (e.g., at least/no more than about 5, 6, 7, 8, 9, 10, 11, 12, 13, 14, or 15 feet above the floor). The collection pipe can extend the full length or almost the full length of the room within the interior space (e.g., about 50, 55, 60, 65, 70, 75, 80, 85, 90, 95, or 100 percent of the length or width of the enclosed space). The collection pipe can include any suitable diameter 33, such as about 15-30 inches (e.g., at least/no more than about 15, 16, 17, 18, 19, 20, 21, 22, 23, 24, 25, 26, 27, 28, 29, or 30 inches). The term "diameter" refers to the longest straight-line distance that passes from side to side through the center of a body. The collection pipe can include any suitable length 34, such as about 5-20 feet or more. It should be appreciated that the collection pipe diameter and length are not limited to the ranges given above.

Figure 3B:
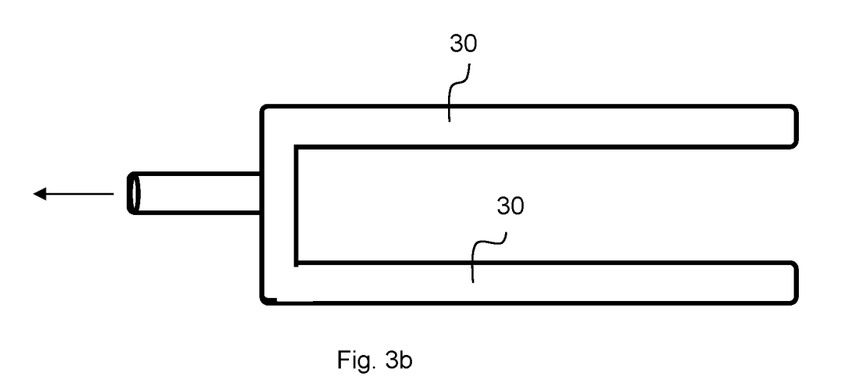
FIG. 3b is a perspective view of a forked collection pipe in accordance with some embodiments of the presently disclosed subject matter.

In some embodiments, the system includes a single collection pipe 30 centered in an enclosed space. In other embodiments, the system can include two or more collection pipes distributed adjacent to the ceiling, as shown in FIG. 3b. In other embodiments, the plurality of collection pipes can run parallel adjacent to the ceiling. The presence of multiple collection pipes can facilitate movement of air into and through the system.

Figure 3C:
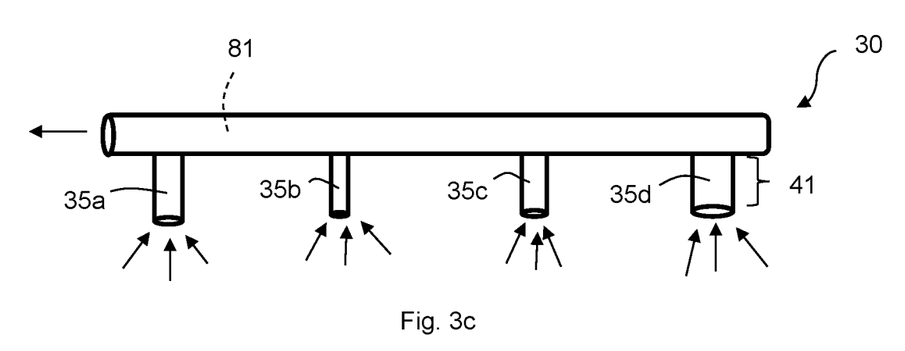
FIG. 3c is a perspective view of a collection pipe with a plurality of nozzles of varying diameters in accordance with some embodiments of the presently disclosed subject matter.

Collection pipe 30 includes a plurality of intake nozzles 35 configured to funnel the air within the enclosed space into the interior of the collection pipe, as shown by the arrows in FIG. 3c. The term "nozzle" broadly refers to any device that controls the distribution and flow of air. The nozzles can function as negative pressure air collection ducts that move air from the interior of enclosed space 10 through the HVAC system as described herein. Specifically, each nozzle is configured on a lower face of the collection pipe (e.g., facing floor 12). As explained in detail below, each nozzle is configured to be placed within a particular zone in the enclosed space. In this way, in each zone, air is routed from a first pair of low velocity diffusers towards the center of its zone, encounters human thermal plumes, is heated, then rises in a vertical direction to a designated nozzle in that same zone. As a result, air within the enclosed space has minimal or no mixing between zones.

Each nozzle 35 varies with respect to at least one other nozzle. For example, first nozzle 35a can have a diameter of about 12 inches, second nozzle 35b can have a diameter of about 10 inches, third nozzle 35c can have a diameter of about 12 inches, and fourth nozzle can have a diameter of about 14 inches. Thus, each nozzle can have a diameter of about 10-20 inches (e.g., at least/no more than about 10, 12, 14, 16, 18, or 20 inches). In some embodiments, each nozzle differs in diameter compared to at least one other nozzle. In some embodiments, each nozzle differs in diameter from all the other nozzles (e.g., each nozzle has a unique diameter). It has been surprisingly found that nozzles with varying diameters function to draw air effectively into the collection pipe compared to nozzles that have uniform diameters. The diversity in nozzles 35 allow the contaminated air at the ceiling to be efficiently funneled into the collection pipe before this air has a chance to fall back down on occupants in the enclosed space. Air flowing from the enclosed space into the negative pressure collection pipe will always follow the path of least resistance. For a collection manifold with equal diameter nozzles, the flow path of least resistance is through the first nozzle (e.g., the nozzle closest to the HVAC return). The higher flow rate of air through the first nozzle causes a decrease in the suction pressure available at all downstream nozzles and as a result, reduces how much air downstream nozzles can pull (the air flow through a nozzle is directly proportional to the square root of the pressure drop). Therefore, reducing the diameter of the first nozzle limits the air flow through this nozzle, increases the suction pressure available at all downstream nozzles, and thereby increase the amount of air downstream nozzles can pull. Hence, there is a set of varying nozzle diameters which leads to maximum capture by the collection pipe, and the negative air pressure inside nozzles creates conducive air flow movement vis-a-vis the thermal plume/currents natural thermal dynamic behavior. The varied nozzles redirect the airflow movement vertically, preventing air saturation or volume build up and eliminating horizontal trajectory of air particulates (e.g., dust, dander, pollen, mold, airborne microorganisms, infectious agents) that can cause illness or disease to room occupants.

Collection pipe 30 can include any suitable number of nozzles 35, such as about 2-10 or more. Thus, the collection pipe can include at least (or no more than) about 2, 3, 15 4, 5, 6, 7, 8, 9, or 10 nozzles. In some embodiments, the number of nozzles corresponds to the number of zones within the enclosed space (e.g., one nozzle per zone).

Each nozzle can have length 41 of about 5-12 inches (e.g., at least/no more than about 5, 6, 7, 8, 9, 10, 11, or 12 inches).

Figure 3D:
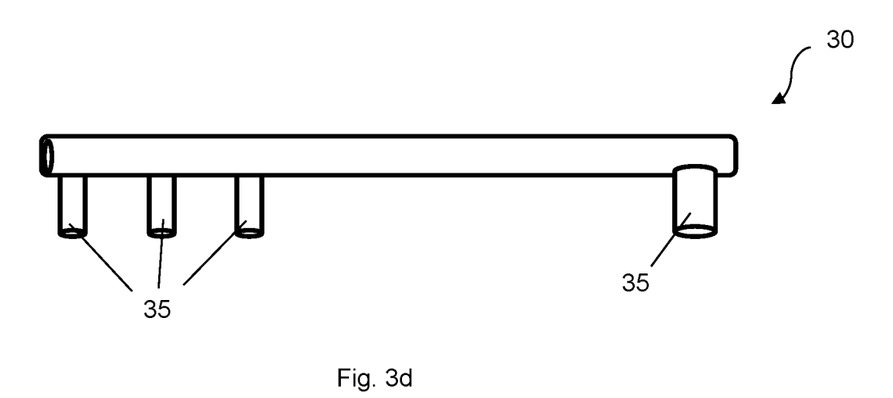
FIG. 3d is a perspective view of a collection pipe with a plurality of clustered nozzles in accordance with some embodiments of the presently disclosed subject matter.

Nozzles 35 can be uniformly distributed along the length of collection pipe 30, as shown in FIG. 3a (e.g., the distance between two nozzles is consistent for all nozzles). Alternatively, the nozzles can be configured in a clustered arrangement along the pipe, as shown in the embodiment of FIG. 3d. In a clustered arrangement, the isolated nozzle can balance the clustered nozzles to create a uniform air flow.

Nozzles can be configured with any desired cross-sectional shape, such as (but not limited to) round, oval, square, rectangular, triangular, and the like.

Collection pipe 30 and nozzles 35 can be constructed from any suitable material, such as (but not limited to) metal (e.g., steel, stainless steel, aluminum, copper), plastic, ceramics, carbon fiber, or combinations thereof.

In some embodiments, air that has been routed from the enclosed space via collection pipe 30 can be mixed with fresh outside air 80 to control carbon dioxide concentrations within the enclosed space. "Fresh outside air" refers to air from outside the enclosed space (e.g., from the exterior of a building, the external environment, or any air not within a confined space). The fresh air can be added on demand and monitored/controlled via pressure control valve 85. Prior to entering the air handler, a fresh air ventilation duct can be used to deliver a predetermined amount of fresh air (e.g., outside air) from a direct open air source or from an existing conditioned air supply of an HVAC system. The fresh air can mix with the collected air from enclosed space 10 to form an isolated air stream that is drawn by vacuum into the air handler. It should be appreciated that a user can control the amount of outside air that mixes with air routed from the enclosed space. For example, a user can stop the flow of outside air completely or can allow a desired amount of outside air to be mixed with the air routed from the enclosed space.

Second end 32 of the collection pipe is in fluid communication with air handler 45 via standard ductwork. For example, ductwork can connect the second end of the collection pipe to the air handler. As such, air collected from the enclosed space is routed through the air handler for treatment. The term "air handler" refers to any element that can treat air within an HVAC system. In some embodiments, air handler 45 can include or cooperate with an indoor blower and motor, as well as indoor refrigerant coil to provide cooling or heating in conjunction with an outside air conditioner or heat pump unit. The air handler can also optionally include a supplemental heat source such as an electric strip heater or a hydronic hot water coil. In some embodiments, the air handler can include a gas furnace unit that also includes an indoor blower and motor, capable of delivering heat by combusting a fuel such as natural gas or propane.

Figure 4:
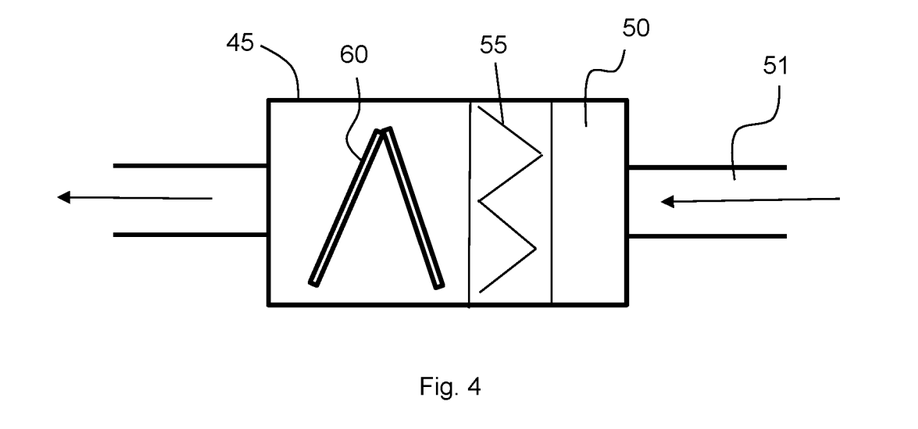
FIG. 4 is a side plan cutaway view of an air handler in accordance with some embodiments of the presently disclosed subject matter.

One embodiment of air handler 45 is illustrated in FIG. 4. As shown, return air is routed from the interior of enclosed space 10 via the collection pipe and associated duct 51 to the air handler. In some embodiments, the air handler can include UV light source 50. Ultraviolet (UV) light represents the frequency of light between 185 nanometers (nm) and 400 nm and is invisible to the naked eye. Within the UV spectrum lie three distinct bands of light: UV-A, UV-B, and UV-C. UV-A light (315 nm to 400 nm) refers to what is commonly called "black light." UV-B light (280 nm to 315 nm) is the type of light that causes sunburn. UV-C light (185 nm to 280 nm) is effective in microbial control. Research has demonstrated that UV-C light between 254 nm and 265 nm is most efficient for microbial destruction. Germicidal lamps that produce the majority of their output in this range are the most effective in microbial control and destruction.

UV light source 50 can include a bulb of any type that produces a disinfecting UV light. Thus, the light source can comprise a UV lamp (e.g., mercury discharge lamp), LED light source, and the like. The UV light source can be positioned such that air entering or passing through air handler 45 is exposed to the produced UV-C light, and the contaminated air is effectively disinfected by the UV rays. Specifically, UV-C light damages the DNA of microorganisms, destroying their ability to replicate and thus rendering them non-infectious. The UV light source ensures that harmful microorganisms (such as bacteria, viruses and the like) passing through the air handler are disinfected before being reintroduced into the enclosed space.

The UV-C treated air can then pass through air filter 55 within the air handler. The filter can function to remove particulates from the air. Filters having various MERV ratings may be employed. For example, a MERV-11 filter can trap mold, dust, pet dander, dust mites, and other allergens with an average efficiency of approximately 65-79.9% for particles 1.0 to 3.0 microns in size. A higher MERV rating results in increased efficiency in capturing air particles. For example, in some embodiments, about 95% collection efficiency can be achieved.

Air filter 55 can comprise any suitable material, such as (but not limited to) polyethylene fibers, polypropylene fibers, fiberglass, polyester, activated charcoal, sorbent materials (e.g., activated carbon, treated carbon, alumina, silica gel, molecular sieves), electrostatic materials (e.g., silver, copper, aluminum, tungsten, platinum, lead, calixarenes), or combinations thereof. In some embodiments, the air filter can be a high efficiency particulate arrester (HEPA) filter or an ultra-low penetration (ULPA) filter.

Air handler 45 also includes coils 60 that provide heating or cooling to the enclosed space. The coils can be heated or cooled by electrical elements or by circulating liquid or steam within the coils, as is well known in the art.

It should be appreciated that the elements of the air handler can be configured in any order. For example, air routed from the collection pipe can first pass through filter 55, then be heated or cooled, and then be exposed to the UV light source. In other embodiments, the air enters the air handler, is filtered, exposed to the UV light source, and then is heated or cooled. In still other embodiments, the air can be exposed to UV-C light, filtered, and then heated/cooled. Filtering, exposure to the UV light source, and heating/cooling can be accomplished in any order.

Figure 5:
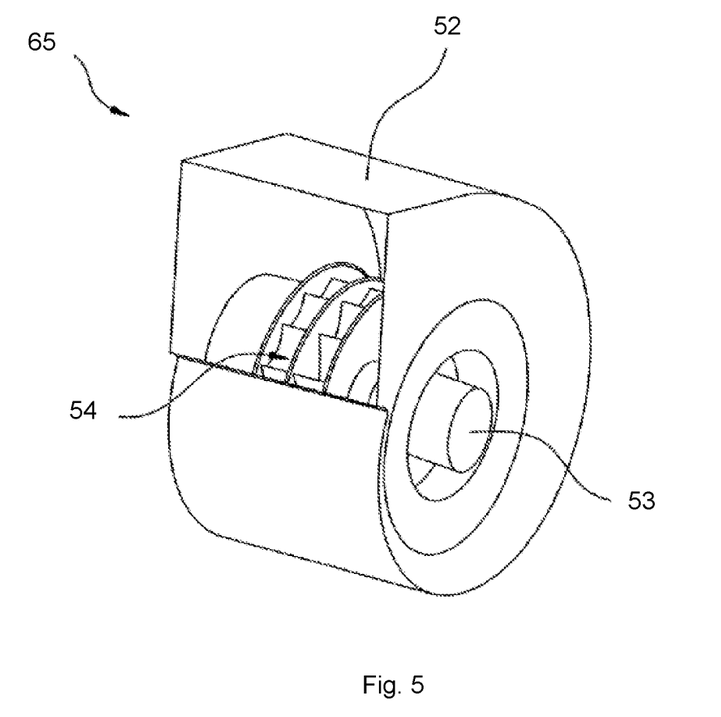
FIG. 5 is a perspective view of a HVAC fan in accordance with some embodiments of the presently disclosed subject matter.
Figure 6A:
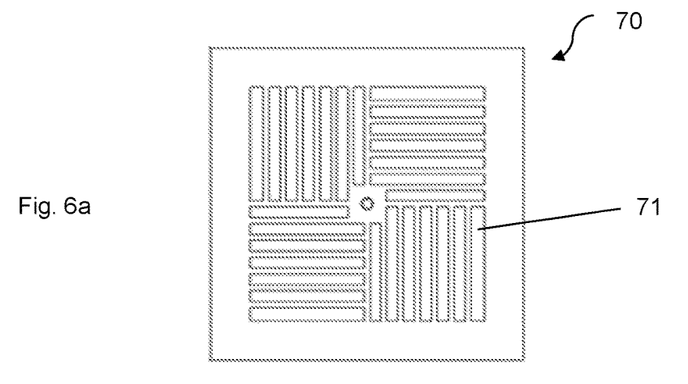
FIG. 6a is a top plan view of a diffuser in accordance with some embodiments of the presently disclosed subject matter.

System 5 also includes one or more booster fans 65 that draw air through the system. For example, twin modular 230V blowers can be used. FIG. 5 illustrates one embodiment of representative fan 65 comprising housing 52, motor 53, and blower wheel 54. It should be appreciated that any type of fan can be used. When fan 65 is active, it pulls air from the enclosed space and/or the outside environment through the air handler filter and/or coils and back into the positive pressure return ducts via low velocity diffusers 70. The term "diffuser" refers to one or more openings adjacent to a floor of an enclosed space, in fluid connection with the air handler. The term "low velocity diffusers" refers to diffusers that enable airflow of about 400 CFM (cubic feet/minute) or less (e.g., at least/no more than about 400, 350, 300, 250, 200, 150, or 100 CFM). FIG. 6a illustrates one embodiment of diffuser 70 comprising a plurality of openings 71 that allow for air flow of disinfected air back into the enclosed space. The diffusers can be inserted into ductwork tubing.

Figure 6B:
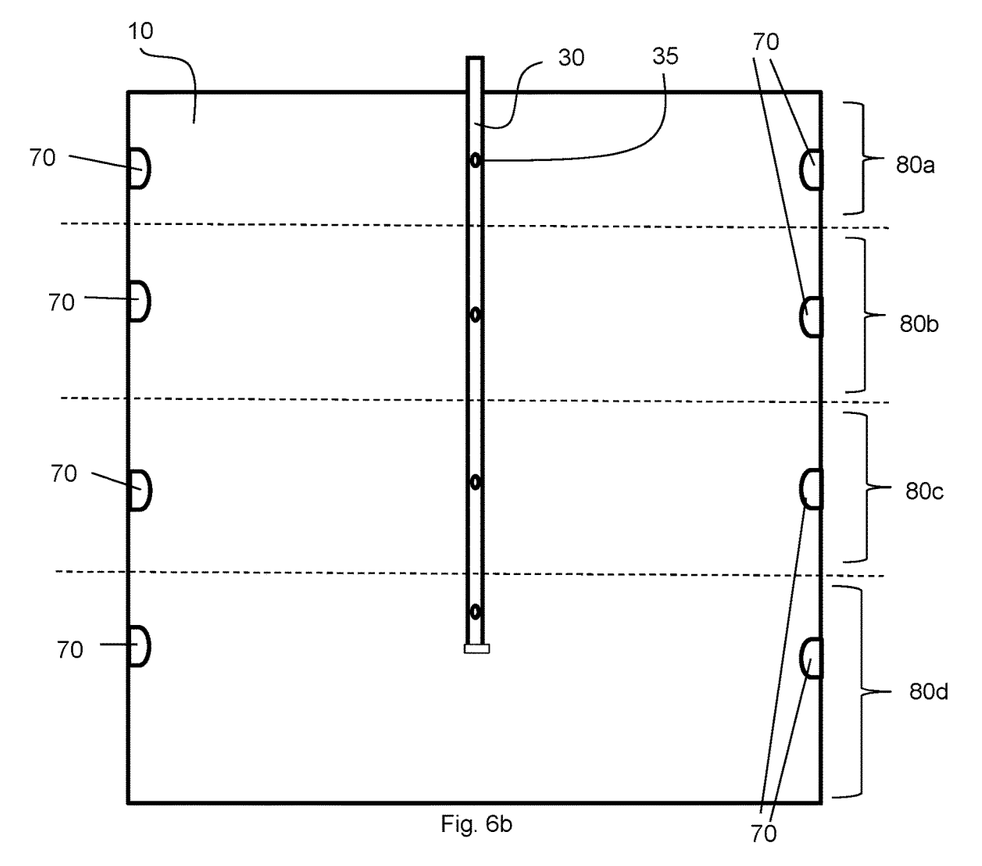
FIG. 6b is a top plan view of an enclosed space comprising a collection pipe and a plurality of low velocity diffusers in accordance with some embodiments of the presently disclosed subject matter.

As shown in FIG. 6b, the diffusers can be oriented adjacent to the floor in enclosed space 10 to create a series of zones. As shown, the spacing of the diffusers creates a plurality of separate zones 80a-80d. The diffusers can be arranged in a parallel orientation, wherein a first diffuser is positioned at the same location on an opposed wall. As a result, a plurality of zones are created, providing vertical air flow into the collection pipe nozzle positioned within that particular zone. In some embodiments, a single nozzle is positioned in each zone. In this way, air is effectively moved through the system and disinfected, and mixing of air between the zones is minimized or eliminated.

In some embodiments, disinfected air can be purged to the atmosphere at 86 prior to passing to diffusers 70. The system can include $CO_2$ controller 90 that is configured to signal the system to purge air to the atmosphere.

The system can optionally further include one or more sensors located inside the enclosed space, and a controller for controlling operation of the system. The controller is in communication with the sensors.

Figure 7:
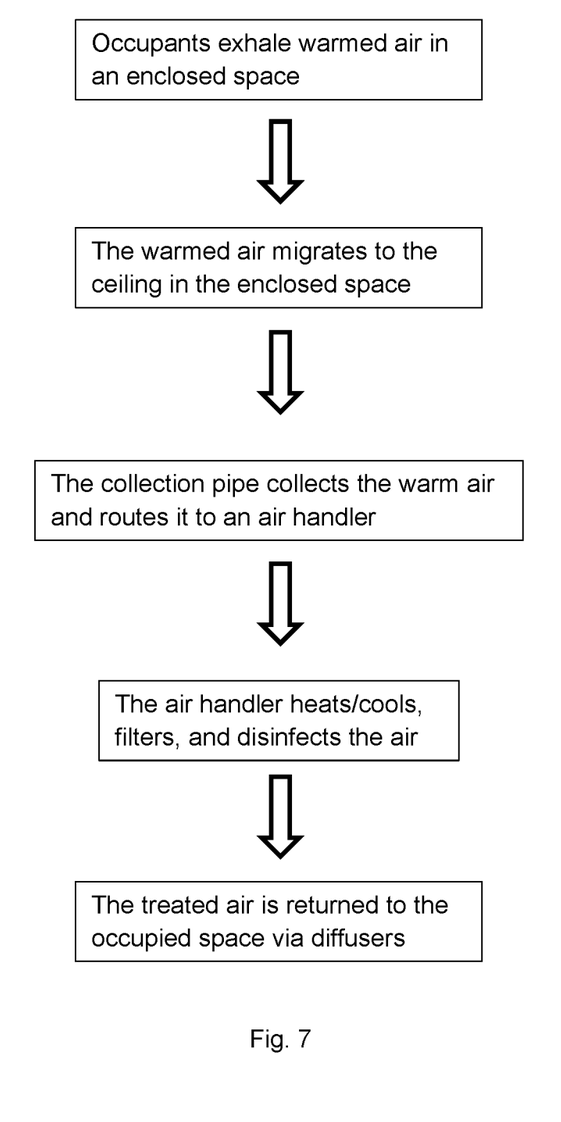
FIG. 7 is a flowchart illustrating one method of using a disinfecting HVAC system in accordance with some embodiments of the presently disclosed subject matter.

In use, occupants present within enclosed space 10 expel air from their lungs while in a 68° F. temperature bath. The air present within the enclosed space can therefore be contaminated with one or more elements, such as harmful microorganisms from the occupants, dust, pollen, pet dander, and the like. The warmed air and any contaminants in the air migrate via zones 80 towards ceiling 11 of the enclosed space. Nozzles 35 of the collection pipe positioned adjacent to the ceiling collect the air and direct it via ductwork to an air handler where the air is disinfected, filtered, and heated/cooled. Specifically, UV-C light can be used to disinfect the air quickly and effectively. The treated air is then transported via one or more fans that direct the air flow through the system to a plurality of positive air flow diffusers positioned at the floor of the enclosed space. The positioning of diffusers 70 create a vertical flow path of air in the enclosed space. Optionally outside air can be drawn through the ductwork and mixed with the warmed air prior to entering air handler 45. Further, disinfected air can be released into the external environment in some embodiments, as shown in the flow chart of FIG. 7.

System 5 thus releases filtered and disinfected air back into enclosed space 10 with a steady and constant operation. The system combines thermal displacement ventilation technology with UV-C light technology to isolate, concentrate, and inactivate contagious pathogens like SARS-Cov-2 in enclosed indoor spaces.

The disclosed system offers many benefits over prior art HVAC systems. For example, the air located within an enclosed space supplied by system 5 is improved due to rising thermal plumes maximized by the variably sized nozzles that carry contaminants and pollutants away from occupants and toward the ceiling collection pipe. The vertically moving air patterns inhibit the transfer of pollutants from one occupant to another. Thus, the disclosed system provides better pollutant removal and enhanced indoor air quality compared to conventional HVAC systems.

System 5 further can be used to inactivate harmful microorganisms, such as the SARS-CoV-2 virus by exposing the air to UV-C light at the effective dose level.

Because the UV-C is housed within the air handler and away from direct human contact and exposure, system 5 is safe to use and will not harm occupants via exposure to UV-C light.

In addition, the presently disclosed subject matter provides a disinfecting HVAC system that is strong, robust, efficient, and durable.

The disclosed system is relatively easy to install in new build homes/buildings and can be easily retrofit to existing HVAC systems.

Exemplary embodiments of the methods and components of the presently disclosed subject matter have been described herein. As noted elsewhere, these embodiments have been described for illustrative purposes only, and are not limiting.

Other embodiments are possible and are covered by the presently disclosed subject matter. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

EXAMPLES

The following Examples provide illustrative embodiments. In light of the present disclosure and the general level of skill in the art, those of ordinary skill in the art will appreciate that the following Examples are intended to be exemplary only and that changes, modifications, and alterations can be employed without departing from the scope of the presently disclosed subject matter.

Example 1

A system was constructed as follows: A collection pipe was constructed from a portion of 304 galvanized steel (24 gauge) with a diameter of 20 inches. The collection pipe had a capacity of about 2000 cfm (cubic feet per minute). The collection pipe included 4 nozzles (10 inches, 12 inches, 12 inches, and 14 inches in diameter). The collection pipe was positioned 12-14 feet above the floor, centered, in an enclosed room. The room also included 8 diffusers positioned at the floor, evenly dispersed along two side walls (e.g., 4 on a first wall and 4 on a second opposed wall). The spacing of the diffusers created 4 separate zones. 6 of the diffusers were Nailor DFR 180B 18×24 low velocity diffusers, 2 of the diffusers were Nailor DFR 90B 30×48 low velocity diffusers.

The collection pipe was operatively connected to a 20 inch return that was in communication with a 5 ton air handler. The air handler included a 25 watt UV-C light (115V). The air handler included a coil. A pair of twin modular blowers (230V) were positioned in fluid connection with the air handler (Canarm 209 Duct Blower 1000 CFM, 2 in sp., BHP=0.66, 1596 RPM).

The blowers were in connection with a 20-inch diameter supply pipe that dispersed the treated air to the 8 diffusers for distribution into the floor of the enclosed space.

The system further included a $CO_2$ controller.

Figure 8:
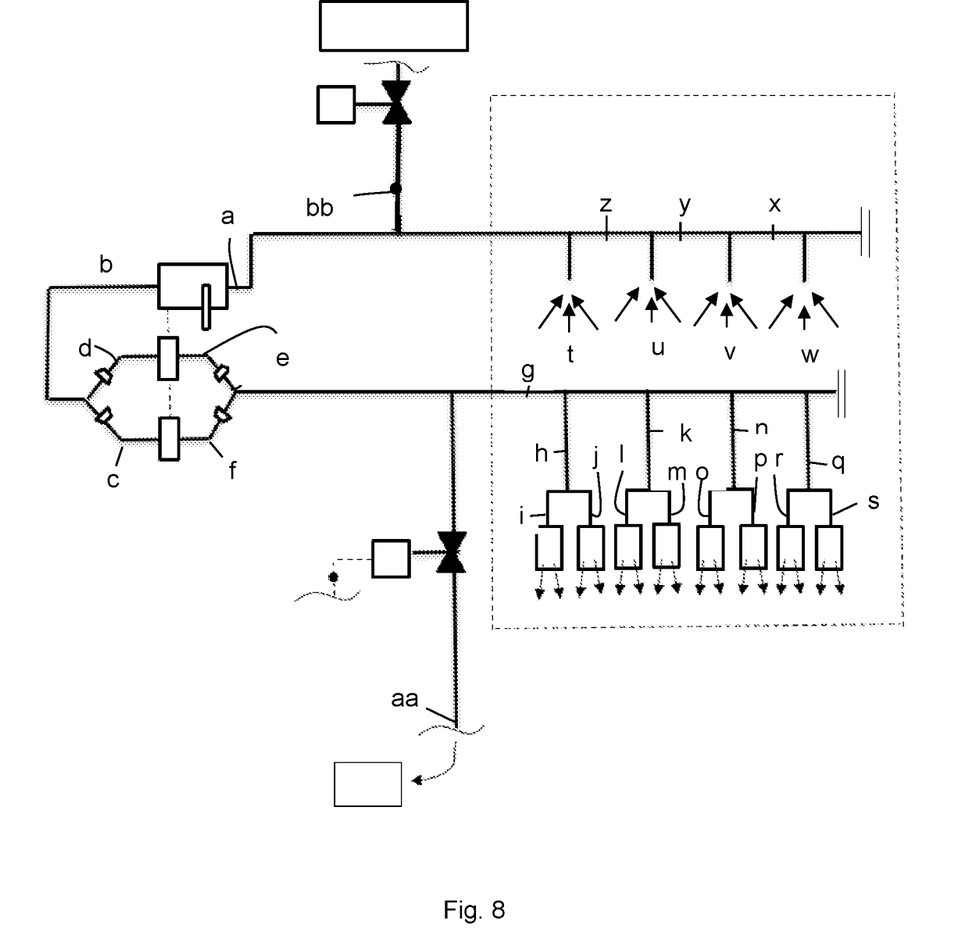
FIG. 8 is a schematic of a diffusing HVAC system illustrating air flow in accordance with some embodiments of the presently disclosed subject matter.

The system was activated, and the temperatures, pressures, and flow rates that resulted in a minimum of 95% collection pipe efficiency, were measured at streams a-bb, as set forth in FIG. 8. The data was collected and is set forth below in Table 1.

| Stream | Service | Temperature (° F.) | Pressure (in-wc) | Flow Rate (CFM) |
|---|---|---|---|---|
| a | Warm air return | 74 | −0.3 to −0.5 | 2000 |
| b | Cold air supply | 55 | −0.3 to −0.5 | 2000 |
| c | Cold air supply | 55 | −0.3 to −0.5 | 1000 |

-continued

| Stream | Service | Temperature (° F.) | Pressure (in-wc) | Flow Rate (CFM) |
|---|---|---|---|---|
| d | Cold air supply | 55 | −0.3 to −0.5 | 1000 |
| e | Cold air supply | 55 | 0.3 to 1.3 | 1000 |
| f | Cold air supply | 55 | 0.3 to 1.3 | 1000 |
| g | Cold air supply | 55 | 0.3 to 1.3 | 2000 |
| h | Cold air supply | 55 | 0.3 to 1.3 | 500 |
| i | Cold air supply | 55 | 0.23 to 1.23 | 250 |
| j | Cold air supply | 55 | 0.23 to 1.23 | 250 |
| k | Cold air supply | 55 | 0.3 to 1.3 | 500 |
| l | Cold air supply | 55 | 0.23 to 1.23 | 250 |
| m | Cold air supply | 55 | 0.23 to 1.23 | 250 |
| n | Cold air supply | 55 | 0.3 to 1.3 | 500 |
| o | Cold air supply | 55 | 0.23 to 1.23 | 250 |
| p | Cold air supply | 55 | 0.23 to 1.23 | 250 |
| q | Cold air supply | 55 | 0.3 to 1.3 | 500 |
| r | Cold air supply | 55 | 0.23 to 1.23 | 250 |
| s | Cold air supply | 55 | 0.23 to 1.23 | 250 |
| t | Warm air return | 74 | 0 | 500 |
| u | Warm air return | 74 | 0 | 500 |
| v | Warm air return | 74 | 0 | 500 |
| w | Warm air return | 74 | 0 | 500 |
| x | Warm air return | 74 | −0.3 to −0.5 | 500 |
| y | Warm air return | 74 | −0.3 to −0.5 | 1000 |
| z | Warm air return | 74 | −0.3 to −0.5 | 1500 |
| aa | $CO_2$ Purge | 55 | 0 to 1.3 | 0 to 1500 |
| bb | Fresh Air Makeup | Ambient | −0.3 to −0.5 | 0 to 1500 |

The data indicates that the system can be effectively used to direct the airflow from the ceiling of an enclosed space through an air handler where the air is disinfected and reintroduced into the enclosed space.

What is claimed is:

1. A disinfecting heating, ventilating, and cooling (HVAC) system comprising:
a collection pipe defined by an interior passageway, a closed first end, an open second end, and a plurality of individual negative pressure nozzles that extend from a lower face of the collection pipe, wherein at least one of the nozzles has a diameter that differs from at least one other nozzle;
an air handler in fluid connection with the second end of the collection pipe, the air handler comprising a UV-C light source, a filter, and heating/cooling coils, wherein air passing through the air handler is exposed to the UV-C light source, passes through the filter, and is heated or cooled;
at least one fan in fluid connection with the air handler, wherein the at least one fan circulates air throughout the system;
a plurality of low velocity diffusers positioned in fluid connection with the at least one fan, wherein the low velocity diffusers are positioned in a floor of an enclosed space and the low velocity diffusers enable airflow of about 100-400 cubic feet per minute;
wherein the plurality of low velocity diffusers are aligned on each side of a pair of opposing walls in the enclosed space to create a plurality of air zones;
wherein at least one nozzle is positioned within each air zone, adjacent to the ceiling of the enclosed space.

2. The system of claim 1, wherein air entering the collection pipe is disinfected after exposure to the UV-C light source, with a 4 log reduction in microorganisms present in the air.

3. The system of claim 2, wherein the microorganisms are selected from influenza virus, coronavirus (SARS-CoV), respiratory syncytial virus (RSV), adenovirus, cytomegalovirus (CMV), Epstein-Barr virus (EBV), dengue virus, rhinovirus, bacteria, or combinations thereof.

4. The system of claim 1, further comprising a port that allows environmental air to be mixed with air exiting the collection pipe prior to entering the air handler.

5. The system of claim 1, further comprising an outlet that allows disinfected air to be exited from the system prior to entering the low velocity diffusers.

6. The system of claim 1, wherein the collection pipe is positioned about 5-15 feet above the floor.

7. The system of claim 1, wherein the collection pipe has a diameter of about 15-30 inches.

8. The system of claim 1, wherein each nozzle has a diameter of about 12-16 inches.

9. The system of claim 1, wherein each nozzle has a unique diameter compared to the other nozzles.

10. The system of claim 1, wherein the nozzles are uniformly distributed about the collection pipe.

11. The system of claim 1, wherein the UV-C light source has a wavelength of about 254 nm to 265 nm.

12. The system of claim 1, wherein the air filter is selected from one or more of polyethylene fibers, polypropylene fibers, fiberglass, polyester, activated charcoal, sorbent materials, electrostatic materials, or combinations thereof.

13. The system of claim 1, wherein the UV-C light source is selected from a UV-C bulb, a UV-C lamp, an LED light, or combinations thereof.

14. A method of disinfecting air in an enclosed space defined by a ceiling and a floor, the method comprising:
routing air adjacent to the ceiling of the enclosed space into the collection pipe of claim 1 via the plurality of nozzles;
routing the air from the collection pipe to the air handler and activating the UV-C light source to disinfect the air;
passing the disinfected air through the system and back into the enclosed space via the low velocity diffusers.

15. The method of claim 14, wherein the disinfected air has a 4 log reduction in microorganisms present in the air.

16. The method of claim 15, wherein the microorganisms are selected from influenza virus, coronavirus (SARS-CoV), respiratory syncytial virus (RSV), adenovirus, cytomegalovirus (CMV), Epstein-Barr virus (EBV), dengue virus, rhinovirus, bacteria, or combinations thereof.

17. The method of claim 14, wherein the air is disinfected in about 0.1 seconds by the UV-C light source.

18. The method of claim 14, further comprising mixing the air leaving the collection pipe with outside air prior to routing the air to the air handler.

19. The method of claim 14, further comprising venting the disinfected air to the outside environment prior to routing the air to the low velocity diffusers.

20. The method of claim 14, wherein the UV-C light source is selected from a UV-C bulb, a UV-C lamp, an LED light, or combinations thereof.

* * * * *